United States Patent [19]

Marshall et al.

[11] Patent Number: 4,775,320
[45] Date of Patent: Oct. 4, 1988

[54] METHOD AND APPARATUS FOR MAKING A DENTAL PROSTHESIS AND PRODUCT THEREFROM

[75] Inventors: Howard B. Marshall, 301 W. 53rd St., Apt. 21K, New York, N.Y. 10019; Gordon E. Kaye, Garrison, N.Y.; Ira L. Lopata, Palm Beach, Fla.

[73] Assignee: Howard B. Marshall, New York, N.Y.

[21] Appl. No.: 80,982

[22] Filed: Aug. 3, 1987

Related U.S. Application Data

[62] Division of Ser. No. 903,641, Sep. 2, 1986, Pat. No. 4,713,005.

[51] Int. Cl.$^4$ .............................................. A61C 5/00
[52] U.S. Cl. .................................... 433/214; 433/180
[58] Field of Search ............... 433/181, 182, 183, 184, 433/40, 37, 214, 213

[56] References Cited

U.S. PATENT DOCUMENTS

| | | | |
|---|---|---|---|
| 1,369,509 | 2/1921 | Weintraub | 433/180 |
| 2,315,748 | 4/1943 | Thompson | 433/40 |
| 3,641,670 | 2/1972 | Karageorge | 433/180 |

FOREIGN PATENT DOCUMENTS 377984  8/1932  United Kingdom .................. 433/40

Primary Examiner—Robert Peshock
Attorney, Agent, or Firm—Lerner, David, Littenberg, Krumholz & Mentlik

[57] ABSTRACT

An apparatus for making and method for forming a dental prosthesis in situ in an edentulouos space defined either adjacent to two existing teeth or between a fixed tooth and a second tooth posterially positioned with respect to the first tooth, and lightly touching the associated gum surface, utilizes a bridge bar assembly having at least one shaped connecting member to be adjustably mounted and connected in the drilled grooves of adjacent teeth, a boss on the bridge bar assembly, and a pontic base adjustably mounted on the boss such that when the bridge bar assembly is in assembled position in the edentulous space for connection to the teeth, the pontic base lightly touches the gum, two spaced mold halves can be placed on the buccal and lingual sides of the edentulous space in which the bridge bar assembly is mounted, (or alternatively, two mold halves with predetermined holes to receive each end of the bridge bar and to permit retention and packing of plastic or pontic forming material), the pontic base can be adjusted relative the associated gum surface to fix the connecting member for the bridge bar assembly relative the drilled section of the teeth, and the edentulous space between the mold halves can be filled with a pontic forming material to form the pontic surrounding the boss on the bridge bar assembly; making the pontic forming material catalytically or chemically set; removing the mold halves; removing the assembly and polishing the sides and undersurface of the pontic or pontics; partially filling the grooves with a filler material; cementing the connecting member in the drilled grooves of the teeth to secure the pontic or pontics in the edentulous space; and applying a cosmetic veneer to the formed pontic or pontics.

17 Claims, 6 Drawing Sheets

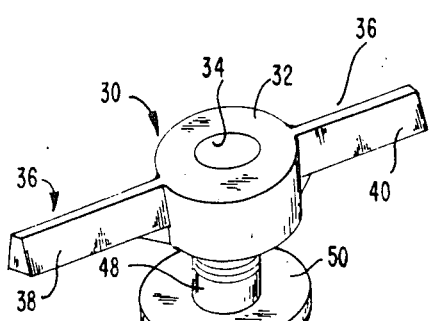
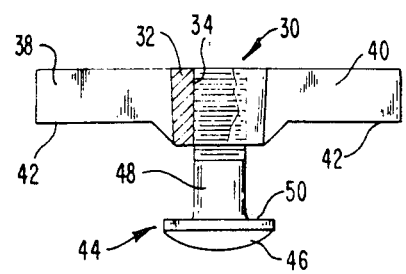
FIG. 1
FIG. 2
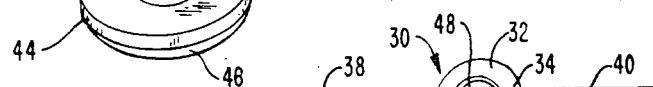
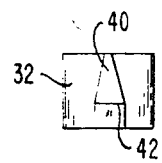
FIG. 3
FIG. 4
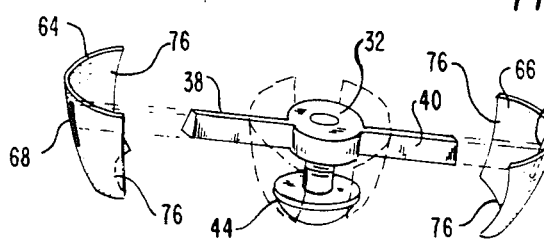
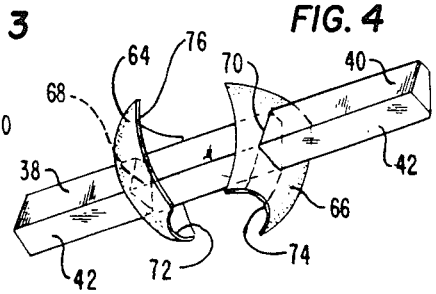
FIG. 5
FIG. 6
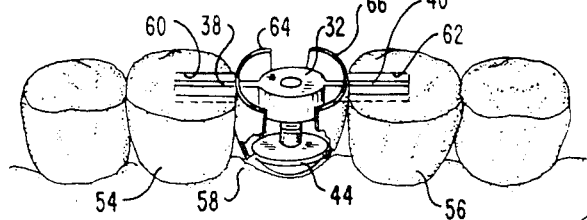
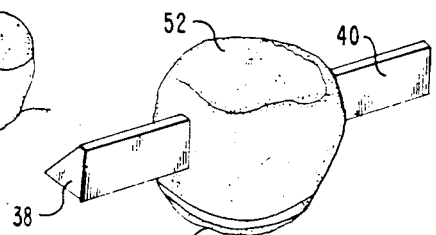
FIG. 7
FIG. 9
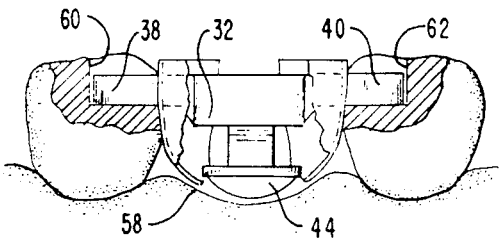
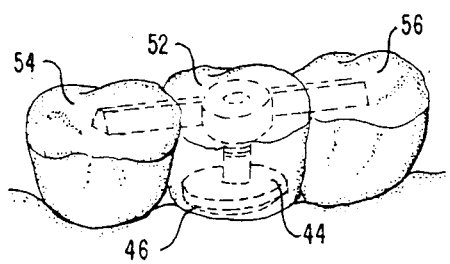
FIG. 8
FIG. 10

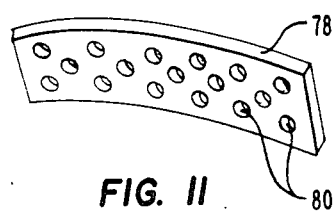
FIG. 11
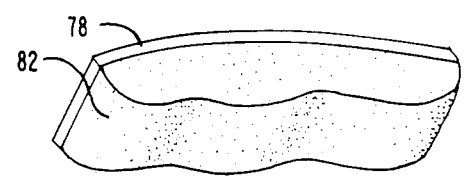
FIG. 12
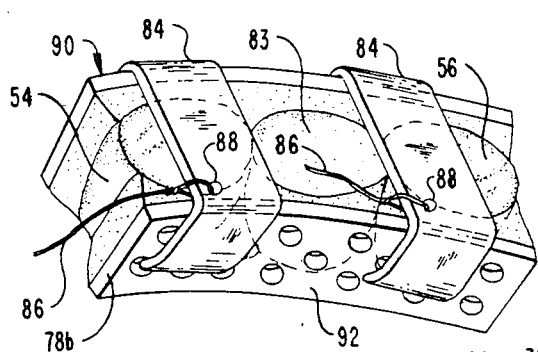
FIG. 13
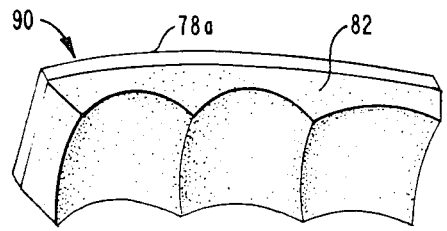
FIG. 14
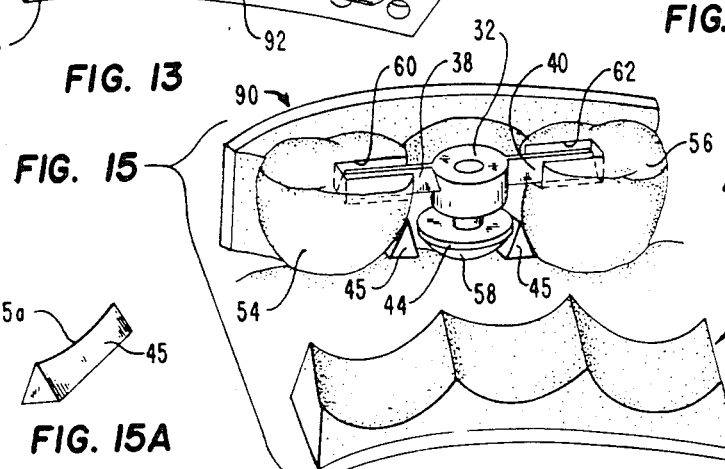
FIG. 15
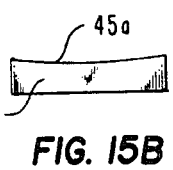
FIG. 15B
FIG. 15A
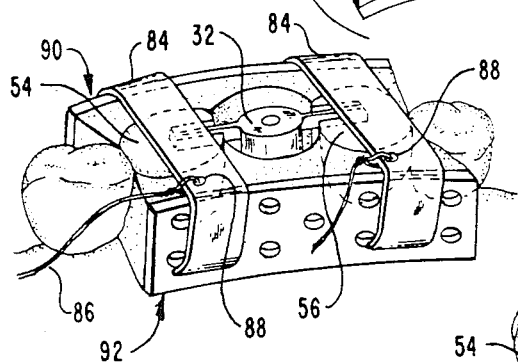
FIG. 16
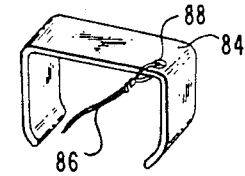
FIG. 17
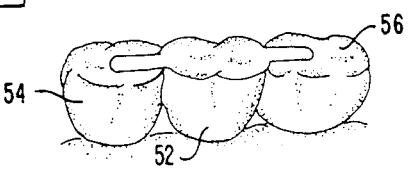
FIG. 18

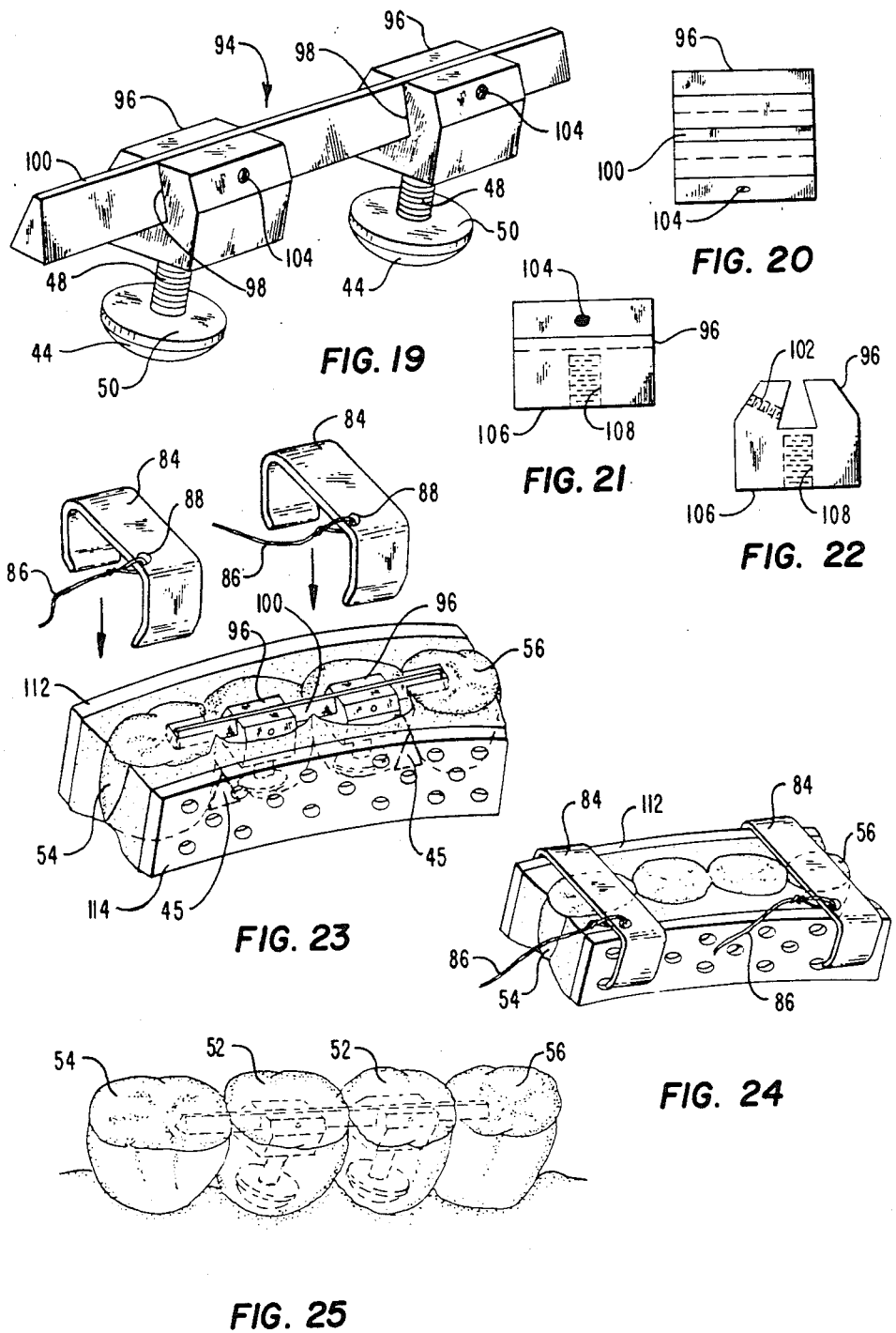

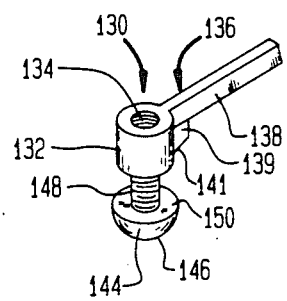
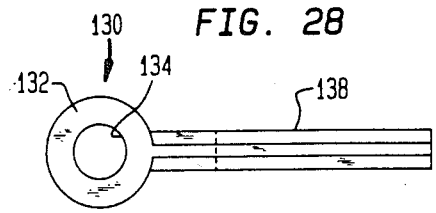
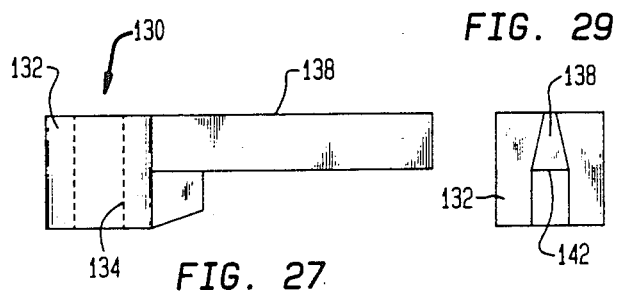
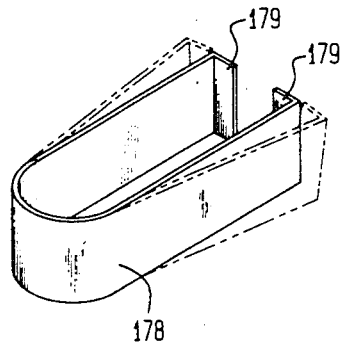
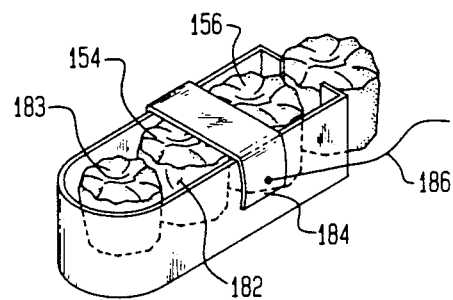
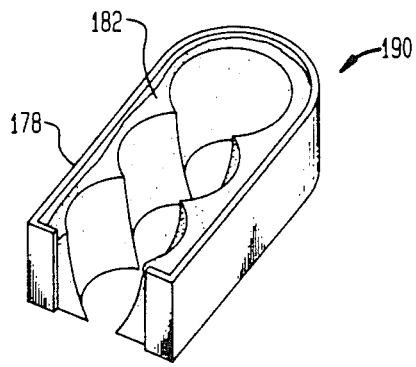
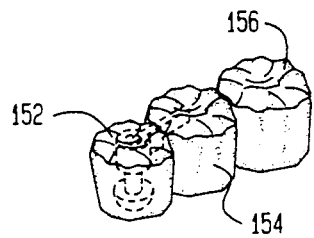

METHOD AND APPARATUS FOR MAKING A DENTAL PROSTHESIS AND PRODUCT THEREFROM

This is a division, of application Ser. No. 903,641, filed 9/2/86 and now U.S. Pat. No. 4,713,005 issued 12/15/87.

BACKGROUND OF THE INVENTION

The present invention relates generally to a method and apparatus for constructing a pontic or pontics to fill an edentulous space adjacent to existing teeth or between two existing teeth and, more particularly, is directed to a method and apparatus for making a pontic or pontics in situ, with minimal adjustments, in one visit.

The formation or fabrication of a dental bridge to span a gap between two teeth, with one or more pontics, or to replace a missing tooth using a cantilevered pontic applied to one or more teeth, is well known in the art. The most common method of replacing a missing tooth or teeth is termed fixed coverage. Generally, the tooth or teeth adjacent to the missing tooth or teeth are ground down, and this usually requires anesthesia. Thereafter, an impression is taken of the missing tooth or teeth and the adjacent teeth by use of dental impression trays. An interim plastic dental prosthesis or bridge is then usually formed to cover the prepared teeth. This generally completes the end of the first visit with the dentist.

The impressions are then sent to a laboratory, where a set of model teeth are formed from the impressions made with the impression trays. A bridge framework is constructed at the laboratory to fit over the adjacent teeth and to provide a false tooth or teeth (pontic(s)) between the teeth, from the impressions. This prosthesis framework, or individual copings, is sent back to the dentist, and the patient then, during a second appointment, has the dental framework or copings tested for fit to the ground down teeth. If the framework or copings of the future dental prosthesis does not fit properly, the above procedure may have to be repeated.

Once the dentist gets to the next stage, either with the directly cast framework or after soldering and connecting copings to create a well fitting framework where it is determined that the framework fits properly, the bridge framework is returned to the laboratory for the application of proper tooth color and returned to the dentist for bite adjustment. Once the bite is ground in, the bridge is returned to the laboratory for final glazing and the like. If the final tooth color is wrong, the bridge may have to be sent back to the laboratory for an additional adjustment.

As a result of the above procedure, the patient may experience four to six visits at the dental office to obtain the fixed bridge, at a considerable inconvenience and cost to the patient.

Although various new products continuously appear on the market, utilizing, for example, newer cements or composites for securing the dental prosthesis to the teeth, multiple procedures are still required which take more than one visit.

Another method of forming a dental prosthesis between two teeth is described in U.S. Pat. No. 3,641,670. According to the method described therein, a groove is formed in the occlusal surfaces of the two teeth, facing each other. A bar traverses the edentulous space between the two teeth and the ends are secured within the grooves formed in the teeth. Thereafter, a paste-like filling material is inserted into a hollow tooth mold, and the tooth mold is forced over the bar such that the bar supports the tooth mold. Thereafter, the paste-like filling material is permitted to harden to form a solid tooth structure which is bonded to the bar. The bar, in turn, is cemented within the grooves in the teeth. Then, the tooth mold is removed, revealing the hardened tooth structure that has been formed.

With this system, however, it is extremely difficult to obtain accurate fitting of the formed tooth with respect to the gum surface (or gingiva). As a result, a large space remains between the lower surface of the formed tooth and the gum surface, which can trap bacteria laden and decomposable material generally responsible for tissue irritation and decay of adjacent teeth.

Other U.S. patents which disclose the use of transverse bars or the like between adjacent teeth, for supporting a dental bridge, are U.S. Pat. Nos. 339,958; 446,769; 1,211,494; 1,262,705; 3,369,509; 1,376,645; 1,649,905; 1,688,621; 1,738,460; 2,028,882; 2,213,964; 2,573,804; 2,635,338; 2,672,686; 2,835,034; 3,091,032; 3,442,015; 4,163,318; 4,360,342; 4,380,432; 4,431,415; 4,445,862; 4,457,714 and 4,474,499.

In regard to providing a screw-threaded adjustment of a false tooth, attention is directed to U.S. Pat. No. 3,787,975. However, adjusting the height of a tooth in accordance with the teachings of this patent is extremely complex as is the device for achieving this end.

OBJECTS AND SUMMARY OF THE INVENTION

Accordingly, it is an object of the present invention to provide a method and apparatus for making a dental prosthesis in a relatively simple one visit procedure.

It is another object of the present invention to provide a method and apparatus for making a dental prosthesis in an extremely economical manner, permitting many people who currently cannot afford fixed bridgework to have a missing tooth or teeth replaced with a fixed prosthesis.

It is still another object of the present invention to provide a method and apparatus for making a dental prosthesis which provides an accurate fit between the lower surface of the dental prosthesis and the gingiva.

It is yet another object of the present invention to provide a method and apparatus for making a dental prosthesis without substantially grinding down adjacent teeth.

It is a further object of the present invention to provide a method and apparatus for making a dental prosthesis in which only small grooves are required to be drilled in the occlusal surfaces of adjacent teeth, thereby avoiding endangering the pulp of such teeth.

It is a still further object of the present invention to provide a method and apparatus for making a dental prosthesis in which dental molds specifically configured to the particular patient's mouth are used to form the dental prosthesis.

In accordance with an aspect of the present invention, a method of forming at least one pontic in situ in an edentulous space defined between a first tooth and a second tooth posteriorly positioned with respect to the first tooth and lightly touching the gum surface therebetween, comprises the steps of drilling the distal and occlusal surfaces of the first tooth to form a first groove; drilling the mesial and occlusal surfaces of the second tooth to form a second groove; positioning a bridge bar assembly including at least one boss and a pontic base adjustably mounted on each boss, in the edentulous space such that the bridge bar assembly can be fixedly connected at opposite sides in the first and second grooves; adjusting the at least one pontic base to a position lightly touching the gum surface in the edentulous space; placing a mold about the edentulous space; filling the mold with a pontic forming material to form the at least one pontic surrounding the at least one boss on the bridge bar assembly; making the pontic forming material set; removing the mold; polishing the sides and undersurface of each formed pontic; and cementing the bridge bar assembly in the first and second grooves to secure the at least one pontic in the edentulous space.

In accordance with another aspect of the present invention, for use in forming at least one pontic in situ in an edentulous space between a first tooth and a second tooth, a method is provided of forming a first mold half which is a direct impression of the buccal side of at least one of the first tooth and the second tooth and the buccal side of the at least one pontic to be formed, and a second mold half which is a direct impression of the lingual side of at least one of the first tooth and the second tooth and the lingual side of the at least one pontic to be formed, the method comprising the steps of positioning a tooth forming core in the edentulous space; applying a mold forming material to a first back plate; placing the first back plate with the mold forming material thereon against the buccal side of at least one of the first tooth and the second tooth and the tooth forming core; permitting the mold forming material on the first back plate to harden to form the first mold half; applying a mold forming material to a second back plate; placing the second back plate with the mold forming material thereon against the lingual side of at least one of the first tooth and the second tooth and the tooth forming core; and permitting the mold forming material on the second back plate to harden to form the second mold half.

In accordance with still another aspect of the present invention, a method of forming at least one pontic in situ in an edentulous space defined between a first tooth and a second tooth posteriorly positioned with respect to the first tooth and lightly touching the gum surface therebetween, comprises the steps of drilling the distal and occlusal surfaces of the first tooth to form a first groove; drilling the mesial and occlusal surfaces of the second tooth to form a second groove; positioning a bridge bar assembly including at least one boss and a pontic base adjustably mounted on each boss, in the edentulous space such that opposite sides of the bridge bar assembly can be fixedly connected in the first and second grooves; adjusting the at least one pontic base to a position lightly touching the gum surface in the edentulous space; forming a first mold half which is a direct impression of the buccal side of at least one of the first tooth and the second tooth and the buccal side of the at least one pontic to be formed; forming a second mold half which is a direct impression of the lingual side of at least one of the first tooth and the second tooth and the lingual side of the at least one pontic to be formed; placing the first mold half and the second mold half about the edentulous space; filling the edentulous space between the first mold half and the second mold half with a pontic forming material to form the at least one pontic surrounding the at least one boss on the bridge bar assembly; making the pontic forming material set; removing the first mold half and the second mold half; polishing the sides and undersurface of each formed pontic; and cementing the bridge bar assembly in the first and second grooves to secure the pontic in the edentulous space.

In accordance with yet another aspect of the present invention, an apparatus for forming at least one pontic in situ in an edentulous space defined between a first tooth and a second tooth and lightly touching the gum surface therebetween, comprises a bridge bar assembly including a boss having a screw-threaded aperture therein, pontic base means screw-threadedly received in the aperture of the boss for adjusting the occluso-gingival height of the bridge bar assembly with respect to the gum surface of the edentulous space; and first and second mold half means surrounding the edentulous space for forming the at least one pontic therein.

In accordance with a further aspect of the present invention, a dental prosthesis for forming at least one pontic in situ in an edentulous space between a first tooth and a second tooth and lightly touching the gum surface therebetween, comprises support means disposed for connection at opposite ends respectively with the first tooth and the second tooth, at least one adjustment means adjustably connected on the support means and movable towards and away from the gum surface for adjusting the position of the at least one adjustment means with respect to the gum surface before the support means is fixedly connected in assembled position into the first tooth and the second tooth, and first and second mold half means removably connected on opposite sides of the at least one adjustment means and operatively associated with the at least one adjustment means for enabling at least one pontic to be formed in the edentulous space between the first tooth and the second tooth.

In accordance with a still further aspect of the present invention, a method of forming at least one pontic in situ in an edentulous space defined adjacent at least one tooth and lightly touching the adjacent gum surface, comprises the steps of drilling the occlusal surface of the at least one tooth to form at least one groove; positioning a bridge bar assembly including at least one boss and a pontic base adjustably mounted on each boss, in the edentulous space such that at least one side of the bridge bar assembly can be fixedly connected in the at least one groove; adjusting each pontic base to a position lightly touching the gum surface in the edentulous space; placing mold means about the edentulous space; filling the mold means with a pontic forming material to form the at least one pontic surrounding the at least one boss on the bridge bar assembly; making the pontic forming material set; removing the mold means; polishing the sides and undersurface of each formed pontic; and cementing the bridge bar assembly in the at least one groove to secure the at least one pontic in assembled position.

In accordance with a yet further object of the present invention, an apparatus for forming at least one pontic in situ in an edentulous space defined adjacent at least one tooth and lightly touching the adjacent gum surface comprises, a bridge bar assembly including a boss having a screw-threaded aperture therein, and a pontic base screw-threadedly received in the aperture of the boss for adjusting the occluso-gingival height of the bridge bar assembly with respect to the adjacent gum surface; and mold means surrounding the edentulous space for forming the at least one pontic therein.

The above and other, objects, features and advantages will become readily apparent from the following detailed description of the invention which is to be read in connection with the accompanying drawings.

BRIEF DESCRIPTION OF THE DRAWINGS

FIG. 1 is a perspective view of a bridge bar assembly according to a first embodiment of the present invention;

FIG. 2 is a side elevational view of the bridge bar assembly of FIG. 1, partly in cross-section;

FIG. 3 is a top plan view of the bridge bar assembly of FIG. 1;

FIG. 4 is an end elevational view of the boss and bridge bar of the bridge bar assembly of FIG. 1;

FIG. 5 is a perspective blown-apart view of the bridge bar assembly of FIG. 1 and mold halves according to one embodiment of the present invention;

FIG. 6 is a perspective view of the bridge bar assembly and mold halves of FIG. 5 in an assembled condition;

FIG. 7 is a perspective view showing insertion of the assembled bridge bar assembly and mold halves of FIG. 6 in the edentulous space between two adjacent teeth;

FIG. 8 is a side elevational view, partly in cross-section, of the assembled bridge bar assembly and mold halves of FIG. 7;

FIG. 9 is a perspective view of the bridge bar assembly of FIG. 1 with the formed pontic thereon;

FIG. 10 is a perspective view of the formed pontic assembled in the edentulous space between the two adjacent teeth;

FIG. 11 is a perspective view of a back plate used to form a mold half according to another embodiment of the present invention;

FIG. 12 is a perspective view of the back plate with a mold forming material applied to a surface thereof;

FIG. 13 is a perspective view of two back plates with mold forming material thereon assembled on opposite sides of two adjacent teeth and on opposite sides of a tooth forming core positioned in an edentulous space between the two adjacent teeth;

FIG. 14 is a perspective view of one mold half that is formed after the mold forming material on a back plate sets;

FIG. 15 is a perspective view, in a partly disassembled configuration, showing the bridge bar assembly of FIG. 1 positioned between two teeth and in conjunction with mold halves as shown in FIG. 14;

FIG. 15A is a perspective view of the embrasure forming wedge of FIG. 15;

FIG. 15B is a side elevational view of the embrasure forming wedge of FIG. 15A;

FIG. 16 is a perspective view of the bridge bar assembly of FIG. 1 positioned between two teeth and with both mold halves as shown in FIG. 14 positioned on opposite sides of the two teeth and secured together in assembled position;

FIG. 17 is a perspective view of a securing clamp for securing the two mold halves of FIG. 16 together about the two teeth;

FIG. 18 is a perspective view showing the pontic formed with the apparatus of FIGS. 11–17, and secured to the two adjacent teeth;

FIG. 19 is a perspective view of a bridge bar assembly according to another embodiment of the present invention for forming one or two teeth in an edentulous space between two adjacent teeth;

FIG. 20 is a top plan view of one boss of the bridge bar assembly of FIG. 19;

FIG. 21 is a side elevational view of the boss of FIG. 20;

FIG. 22 is an end elevational view of the boss of FIG. 20;

FIG. 23 is a perspective view, showing assembly of the bridge bar assembly of FIG. 19 in an edentulous space between two teeth and surrounded by two mold halves;

FIG. 24 is a perspective view used for illustrating the formation of two adjacent teeth with the apparatus of FIG. 23;

FIG. 25 is a perspective view showing the formed dental prosthesis in assembled position between the two teeth, with the bridge bar assembly being shown in phantom;

FIG. 26 is a perspective view of a bridge bar assembly according to another embodiment of the present invention;

FIG. 27 is a side elevational view of a portion of the bridge bar assembly of FIG. 26;

FIG. 28 is a top plan view of the bridge bar assembly of FIG. 26;

FIG. 29 is an end elevational view of the boss and bridge bar of the bridge bar assembly of FIG. 26;

FIG. 30 is a perspective view of a back plate used to form the mold according to another embodiment of the present invention;

FIG. 33 is a perspective view of the back plate of FIG. 30 with mold forming material thereon assembled on opposite sides of two adjacent teeth and on opposite sides of a tooth forming core positioned adjacent to one of the teeth;

FIG. 34 is a perspective view of a mold that is formed after the setting of the mold forming material on the back plate of FIG. 31 sets;

FIG. 36 is a perspective view showing the pontic formed with the apparatus of FIGS. 26–33, and secured to two adjacent teeth.

DETAILED DESCRIPTION OF THE PREFERRED EMBODIMENTS

Figure 4A:
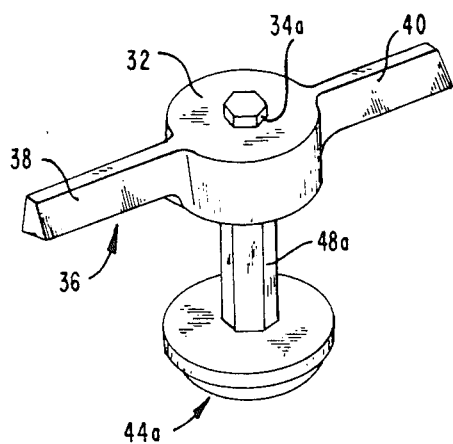
FIG. 4A is a perspective view of a bridge bar assembly according to another embodiment of the present invention.

Referring to the drawings in detail, and initially to FIGS. 1-4 thereof, a bridge bar assembly 30 according to one embodiment of the present invention generally includes a cylindrical boss 32 with a centrally positioned screw-threaded aperture 34 extending entirely therethrough.

Although boss 32 is shown as being of a cylindrical configuration, it will be appreciated that the present invention is not so limited and that boss 32 may include other configurations, such as a square box-like configuration or the like. A bridge bar 36 extends diametrically from opposite sides of boss 32. Specifically, bridge bar 36 is formed of a first bridge bar section 38 extending radially outward from the outer surface of boss 32 and a second bridge bar section 40 also extending radially outward from the outer surface of boss 32 and being diametrically opposite first bridge bar section 38. As shown in FIG. 4, each bridge bar section 38 and 40 has an upwardly tapered or substantially triangular configuration in order to increase the volume of composite or other plastic or toothlike material to be placed next to bridge bar 36, while providing a sufficiently wide lower surface 42 for supporting bridge bar sections 38 and 40 in a stable manner within grooves formed in adjacent teeth, as will be described in greater detail hereinafter. Preferably, first and second bridge bar sections 38 and 40 are formed integrally with boss 32, although such sections may be separately attached to boss 32.

Bridge bar assembly 30 further includes a pontic base 44 having a generally convex shaped lower surface 46. A screw-threaded shaft 48 extends from the upper surface 50 of pontic base 44 and is screw-threadedly received within aperture 34 of boss 32 to permit vertical adjustment of pontic base 44 with respect to boss 32.

Bridge bar assembly 30 is used in a method for forming a pontic (pontics) or false tooth (teeth) between a first tooth and a second tooth posteriorly positioned with respect to the first tooth, said pontic or pontics resting lightly on the gum surface therebetween.

Specifically, and referring now to FIGS. 5-10, a first method of forming a pontic according to the present invention will be described.

In the first embodiment of the present invention, a pontic (or pontics) 52 is formed in situ in an edentulous space defined between a first anterior tooth 54 (or two anterior teeth) and a second tooth 56 posteriorly positioned with respect to first tooth 54 and resting lightly on the gum surface 58 therebetween. Specifically, the distal and occlusal surfaces of first tooth 54 (or two adjacent teeth) are drilled to form a first groove 60, and the mesial and occlusal surfaces of second tooth 56 are likewise drilled to form a second groove 62. Each groove is drilled to an adequate depth. Drilling of the more posterior of the teeth extends through the mesial marginal ridge, and then up to the distal marginal ridge. Drilling of the anterior tooth extends throgh the distal marginal ridge and up to the mesial marginal ridge. A number 35 inverted cone bur or similar bur can be used for drilling the grooves. Each groove 60 and 62 faces the other for receiving the free ends of first and second bridge bar sections 38 and 40, respectively.

Excess lengths of bridge bar sections 38 and 40 are then cut so that the latter can fit within grooves 60 and 62, respectively, as shown in FIG. 8, with pontic base 52 centered between teeth 54 and 56.

In this regard, the lower surface 42 of each bridge bar section 38 and 40 rests on the occlusal floor of the cutaway portion of each tooth which defines grooves 60 and 62. Pontic base 44 is screw-threaded up into the boss 32 so that the base position rests lightly on the gum surface in the edentulous space between first and second teeth 54 and 56, while the lower surface 42 of the bridge bar rests on the occlusal floor of the grooves in the teeth. Preferably, pontic base 44 is screw-threaded down into light contact with the gum surface, as shown in FIG. 8. In this regard, it is noted that pontic base 44 is preferably fabricated from a highly polished metal so as to substantially prevent plaque retention on lower surface 46 thereof.

The means of raising and lowering said pontic base 15 is not to be limited to a screw mechanism but could also be a vertically sliding mechanism, such as a hex, square, rectangular or other odd-shaped shaft 48a which is non-rotatably inserted into a corresponding bore 34a of boss 32 and into pontic base 44a and slid up and down into boss 32, by a friction fit, as shown in FIG. 4A. In either the case of the screw-threaded arrangement of FIGS. 1-4 or the hex-shaped shaft of FIG. 4A, the shaft 48 or 48a could be made to extend above boss 32 to be engaged for turning or sliding movement to move pontic base 44a downward to rest lightly on the gum, when bridge bar 36 is positioned to rest on the occlusal floors of grooves in the adjacent teeth. If a friction fit method is used for vertical adjustment, the shaft is slid gingivally through the bridge bar bore until pontic lower surface 42 rests lightly on the tissue.

Figure 4C:
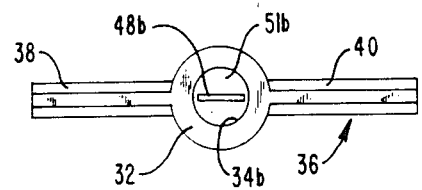
FIG. 4C is a top plan view of the bridge bar assembly of FIG. 4B.
Figure 4B:
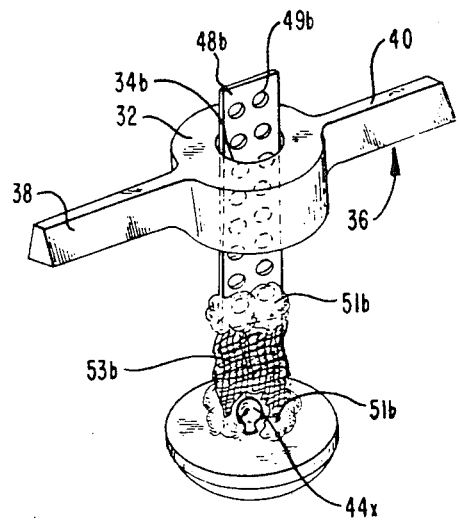
FIG. 4B is a perspective view of a bridge bar assembly according to another embodiment of the present invention.

As still another alternative, as shown in FIGS. 4B and 4C, in addition to the screw-threaded arrangement of FIGS. 1-4, and the friction fitted hex shaft of FIG. 4A, a mechanically held arrangement can be provided. For a lower tooth (or teeth) replacement, a wire or plastic mesh core 53b is attached to pontic base 44b, specifically to nub 44x, and connected via a plastic locking material 51b. The lower surface of pontic base 44 is placed properly positioned on the gingival surface. Bridge bar 40 is positioned in the grooves in the teeth. As shown in FIG. 4C, a flat rectangular metal or plastic locking tab 48b having holes 49b can now be inserted gingivalward through bore 34b of boss 32. Locking tab 48b is slipped downward until its inferior border rests on the superior surface of mesh core 53b.

Now, tab 48b is joined to mesh core 53b via the plastic locking material 51b. Lastly, bore 34b is filled with the plastic locking material 51b to mechanically bond tab 48b within bore 34b, and the portion of tab 48b extending above boss 32 is cut. The above steps apply to forming a lower pontic.

The steps would be reversed for forming an upper pontic in that the pontic base would be attached to mesh core 53b, the mesh core 53b to vertical locking tab 48b, and tab 48b placed loosely through bore 34b. Next, the bridge bar 36 is placed within the tooth grooves and held by soft wax. Holding the pontic base against the gingival edentulous surface, the locking tab 48b is now locked with plastic locking material 51b to mechanically bond tab 48b is now locked with plastic locking material 51b to mechanically bond tab 48b within bore 34b.

It will be appreciated that variations on the embodiments of FIGS. 4B and 4C can be made. For example, tab 48b can be eliminated and replaced entirely by mesh core 53b which may be moved vertically through bore 34b and secured therein by any suitable means, and then trimmed at its upper end. As another example, mesh core 53b can be eliminated, with tab 48b connected directly to pontic base 44b. The important aspect of the invention is that pontic base 44 is vertically adjustable via the shaft so that it rests lightly on the gum before finally securing the shaft to the bridge bar.

In all of the above embodiments, different pontic bases 44 having slightly different convex shaped lower surfaces 46 may be removed from and separately attached to screw-threaded shaft 48, hex-shaft 48a, tab 48b or mesh core 53b, to permit better selection of pontic shapes which relate both to the gum ridge and the adjacent teeth 54 and 56.

Figure 4D:
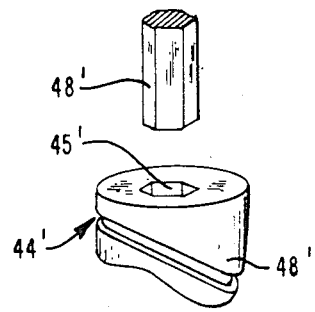
FIG. 4D is a perspective view of a pontic base according to another embodiment of the invention, disassembled from the respective hex shaft.
Figure 4E:
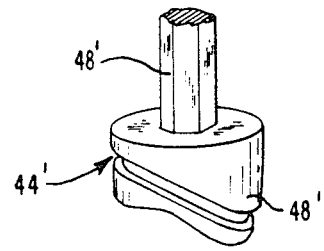
FIG. 4E is a perspective view of the pontic base of FIG. 4D, in assembled condition with the hex shaft.

Alternatively, the lower surface of the pontic base 44' can be flat and/or have a ridge lap 46', as shown in FIGS. 4D and 4E. Ridge lap 46' of pontic base 44' is provided on the buccal side to more accurately permit the composite buildup to simulate a real tooth. Pontic base 44' may be made in an assortment of shapes to account for different ridge shapes. With this embodiment, it is preferable to use a specially created diamond high (or low) speed bur to create a pre-shaped superficial abrasion or indentation in the ridge, which will heal rapidly and when healed, conform to the highly polished undersurface of the pontic base. Ideally, the shape of the portion of the diamond bur which creates the tissue indentation as seen in profile is a long ellipse, and the three-dimensional shape seen in profile is an attenuated oval. As also shown in these FIGURES, pontic base 44' is formed with a bore 45' extending therethrough, whereby a hex shaft 48' can be removably secured thereto.

Returning to placement of the bridge bar assembly, after adjustment of the shaft and pontic base vertically, wax is used at the free ends of first and second bridge bar sections 38 and 40 to secure them in place within grooves 60 and 62, respectively. In addition, a small portion of wax, acrylic or composite can be used around shaft 48 to prevent rotation of the latter within boss 32 after pontic base 44 has been adjusted.

In accordance with the first embodiment of the present invention, two mold halves 64 and 66 are provided, each having an arcuate configuration which, when positioned adjacent each other, form a cavity within which pontic 52 is formed. In this regard, each mold half includes an aperture 68 and 70, respectively, the occlusal most portion which conforms substantially to the occlusal-most cross-sectional configuration of first and second bridge bar sections 38 and 40, and is vertically large enough such that mold halves 64 and 66 may be placed in a gingival direction with one mold half on one side of the boss and the other on the opposite side of the boss, having slid the mold halves onto the bridge bar sections 38 and 40 and positioned in proper relationship to the occlusal level of adjacent teeth, and to the pontic base 44, as shown in FIG. 6. Preferably, as shown in FIG. 5, the lower surfaces of mold halves 64 and 66 are cut away in an arcuate configuration at 72 and 74, respectively, to permit the convex shaped lower surface 46 of pontic base 44 to fit therethrough, as shown in FIGS. 6 and 8. In addition, the side edges 76 of mold halves 64 and 66 are slightly cut away so that, when mold halves 64 and 66 are supported on first and second bridge bar sections 38 and 40, respectively, adjacent side edges 76 are spaced from each other, as shown in FIG. 6. It is noted that the mold halves may take different shapes, but with each mold half having an aperture for receiving the beam and against which the composite or plastic may be packed.

Thus, bridge bar assembly 30 is positioned in the edentulous space between first tooth 54 and second tooth 56 such that the ends of first and second bridge bar sections are positioned and supported within first and second grooves 60 and 62, respectively. Then, bridge bar assembly 30 is adjusted with respect to teeth 54 and 56, as described above, so that mold halves 64 and 66, filled with a plastic material (like a composite resin), are positioned on first and second bridge bar sections 38 and 40, respectively.

Alternatively, as shown in dashed lines in FIG. 6, apertures 68 and 70 can be elongated to the bottoms of mold halves 64 and 66, that is, to arcuate cut-away sections 72 and 74, to form elongated slots 68a and 70a, respectively. Then, each mold half 64 and 66 can be packed with the pontic forming material and vertically push down into position on bridge bar 36, rendering the procedure easier and simpler.

The pontic forming material is then made to set either chemically or catalytically. Thereupon, the formed pontic 52 and bridge bar assembly 30 are removed from teeth 54 and 56, and mold halves 64 and 66 are removed from first and second bridge bar sections 38 and 40, respectively, so that the product shown in FIG. 9 is produced. At this time, any final shaping of pontic 52 is performed, with any flash being polished from the undersurface and sides of pontic 52. It is an important aspect of the present invention to provide removal of the assembly shown in FIG. 9 before cementing it in permanently, so that the underside of pontic base 44 can be polished. The surfaces are polished with discs, burs, pastes or the like. Further, any final color modifications on the buccal side of pontic 52 is made with composites, plastics and available staining techniques. The finished and polished assembly is now ready for final insertion into the mouth of the patient.

Specifically, all wax is removed from the free ends of first and second bridge bar sections 38 and 40 which rest in the occlusal surfaces of grooves 58 and 60, and such occlusal surfaces are likewise cleaned of wax. The finished and polished pontic 52 is now ready for final insertion. A small amount of composite paste is placed on the occlusal surfaces within grooves 60 and 62 to fix the free ends of first and second bridge bar sections 38 and 40 therein. This is then chemically or catalytically cured. Additional composite is then placed over the exposed bridge bar sections 38 and 40 so as to fill grooves 60 and 62.

A thin flexible, non-adhesive "Saran" wrap-like material is then placed over the opposing tooth. The patient then bites down to obtain an exact imprint of the occlusal surface of the opposing tooth. The "Saran" wrap-like material is removed and the composite is made to set chemically or catalytically ("light cure"). The bite is adjusted by removing any excess from the occlusal surface of pontic 52 with finishing burrs, and then polishing the same, to produce the result shown in FIG. 10.

With the present invention according to the first embodiment, the entire procedure of forming a dental bridge can be performed in a single visit, without the requirement of any laboratory work, with reduced time and with a greatly reduced cost savings for the patient up to 60% from conventional methods. In addition, accurate adjustment of the undersurface of pontic 52 is achieved with pontic base 44.

Referring now to FIGS. 11-18, there is shown a second embodiment of the present invention, in which elements similar to those in the first embodiment of FIGS. 5-10 are represented by the same numerals, and a detailed description thereof will be omitted herein for the sake of brevity.

In accordance with the second embodiment, the same bridge bar assembly 30 is used, but in conjunction with different mold halves. Specifically, in order to form the mold halves according to the second embodiment of the present invention, a perforated flexible backing plate 78, which is at least 1.25-1.5 inches long is provided for forming each mold half. Each perforated backing plate 78 has a slightly arcuate configuration, thereby conforming to the arcuate arrangement of first tooth 54, second tooth 56 and the pontic to be formed therebetween. Each perforated backing plate 78 also includes a plurality of apertures 80 therein.

In accordance with the present invention, for forming the mold half on the lingual side of teeth 54 and 56, a mold forming material 82, such as silicone, rubber, polysiloxane or any other impression material, is applied to the convex inner surface of a backing plate 78 (the lingual mold) with a thickness of, for example, 3 mm, and for forming the other mold half on the buccal side of teeth 54 and 56, the same mold forming material 82 is positioned on the concave surface of a second backing plate 78. Hereinafter, the buccal side backing plate will be referred to by numeral 78a and the lingual side backing plate by numeral 78b.

Before applying mold forming material 82 to plates 78a and 78b, however, two embrasure forming wedge 45 (FIG. 15A), shaped specifically to provide adequate cleansing space upon their removal, are placed on the mesial surface of the distal or posterior tooth 56, at the gingiva, and on the distal surface of the front or mesial tooth 54 at the gingiva. These wedges are tack bonded onto the teeth 54 and 56 after being shaped to curve slightly onto the buccal and lingual surfaces thereof.

A tooth forming core 83 is then positioned within the edentulous space between first and second teeth 54 and 56 and held by wax to teeth 54 and 56. Tooth forming core 83 may be a preformed core chosen from a number of different configurations. Alternatively, tooth forming core 83 can be formed from a ball of wax configured in the approximate shape of the pontic 52 to be formed.

Thereafter, backing plates 78a and 78b with the mold forming material 82 thereon are positioned against the buccal and lingual sides of first and second teeth 54 and 56 and tooth forming core 83, as shown in FIG. 13. U-shaped metal clamps 84 extend over the occlusal surfaces of teeth 54 and 56 and engage the free surfaces of backing plates 78a and 78b to secure the latter against the buccal and lingual sides of first and second teeth 54 and 56 and tooth forming core 83. The ends of clamps 84 are preferably bent inwardly to better grip backing plates 78a and 78b. Further, in order to better grip plates 78a and 78b, the mold forming materal may also be placed on the sides thereof facing away from the teeth before placing the clamp. In addition, a lanyard 86 is secured within an aperture 88 of each clamp 84 to readily permit removal of clamps 84 from the mouth of the patient and to prevent swallowing the clamp. The mold forming material on backing plates 78a and 78b is then permitted to set for approximately three minutes or slightly longer, whereupon clamps 84 are removed to permit removal of the formed buccal mold half 90 and lingual mold half 92. To prevent the mold forming material 82 from sticking on the surfaces of teeth 54 and 56 and tooth forming core 83, the latter can be painted with an oil.

Thereafter, tooth forming core 83 is removed, and grooves 60 and 62 are formed in teeth 54 and 56 in the identical manner as described in the first embodiment of FIGS. 5-10. Bridge bar assembly 30 is then positioned in the edentulous space such that first and second bridge bar sections 38 and 40 are positioned and supported within grooves 60 and 62, respectively. Then, pontic base 44 is screwed occlusally, or slid occlusally up into the boss, and adjusted until the undersurface of pontic base 44 rests lightly on the gum surface in the edentulous space between teeth 54 and 56. Preferably, the pontic base can be adjusted by sliding or turning element 48 where it extends occlusally through the boss, and adjusting it gingivally. A small amount of wax can be used to secure first and second bridge bar sections 38 and 40 within grooves 60 and 62, respectively.

With bridge bar assembly 30 so positioned, as shown in FIG. 15, embrasure forming wedges 45 are inserted at the gum level between pontic base 44 and adjacent teeth 54 and 56. As shown in FIGS. 15A and 15B, each embrasure forming wedge 45 has a triangular cross-sectional configuration and is formed with a concave upper surface 45a. Such embrasure forming wedges aid in more accurately defining the pontic to be formed. Buccal and lingual mold halves 90 and 92 are then positioned about first and second teeth 54 and 56 and about the edentulous space therebetween. Then, U-shaped clamps 84 again are inserted about mold halves 90, 92 to clamp the same about first tooth 54 and second tooth 56, as shown in FIG. 16. The edentulous space between first and second teeth 54 and 56 and between mold halves 90 and 92 is then filled gradually with a pontic forming material, such as a plastic, or resin composite paste, made to set until the material extends above the occlusal surfaces of teeth 54 and 56, to form a pontic 52 surrounding boss 32 on bridge bar assembly 30. After the pontic forming material is permitted to chemically or catalytically set to form pontic 52, U-shaped clamps 84 and mold halves 90 and 92 are removed. The bridge bar with pontic base are now removed and the flash (excess plastic or composite) removed and the sides and undersurface of the pontic base polished as previously described. At this time, any final color modifications on the buccal side can be made with the composite paste, or by available staining techniques.

Accordingly, pontic 52 is formed surrounding bridge bar assembly 30, as shown in FIG. 9, and is assembled with respect to first and second teeth 54 and 56 in an identical manner to that previously described with respect to the first embodiment of FIGS. 5-10, with the additional step of removing the aforementioned embrasure forming wedges. The end result is shown in FIG. 18. Another way of forming the pontic is only using the lingual backing plate, finger held, and embrasure forming wedges, and building up the composite toward the buccal side by hand, shaping and curing as one builds up. Final color modifications and staining are handled the same way.

It is noted that, with both of the first and second embodiments described above, a single pontic 52 is formed for filling a one tooth edentulous space. However, it is possible to utilize the invention of the first and second embodiments with respect to a situation where there is a two tooth edentulous space.

Referring now to FIGS. 19-25, there is shown a third embodiment of the present invention, in which elements similar to those described above with respect to the first and second embodiments will be identified by the same reference numerals, and a detailed description thereof will be omitted herein for the sake of brevity.

Referring first to FIG. 19, a modified bridge bar assembly 94 generally includes at least one boss 96 of a generally rectangular configuration and having a slot 98 extending entirely therethrough, in the lengthwise direction thereof, for receiving a single bridge bar 100. Preferably, bridge bar 100 has a substantially triangular cross-sectional configuration as with bridge bar 36, and each slot 98 has a similar configuration. In this manner, each boss 96 is supported and can be slid along bridge bar 100. Further, one side wall of each boss 96 includes a screw-threaded aperture 102 extending entirely therethrough, and a set screw 104 is screw-threadedly received within each aperture 102. In this regard, set screw 104 can be screwed into engagement with bridge bar 100 to retain the respective boss 96 on bridge bar 100 in a fixed position. The lower surface 106 of each boss 96 includes a screw-threaded aperture 108, and a pontic base 44 which is identical to pontic base 44 of the first two embodiments has a screw-threaded shaft 48 extending from the upper surface 50 thereof screw-threadedly received within the aperture at the lower surface of each respective boss 96. Generally, bridge bar assembly 94 is more versatile than bridge bar assembly 30, since it readily permits more than one boss 96 thereon and provides adjustment of each boss in the lengthwise direction with respect to bridge bar 100. Alternatively, one boss may be fixed and the other one movable on bridge bar 100. The external shape of the boss may vary.

In accordance with the third embodiment, a buccal mold half 112 and a lingual mold half 114 are formed in the same manner as described in the second embodiment with respect to mold halves 90 and 92, the difference being that, in the third embodiment, a two tooth edentulous space area is covered by mold halves 112 and 114.

To form the dental prosthesis, bridge bar assembly 94 is positioned within the edentulous space between first tooth 54 and second tooth 56. Where there are two abutment teeth adjacent on either side of the edentulous space, it is preferable to have bridge bar 100 longer, passing into both teeth, be they posterior and/or anterior to the space.

Then, each boss 96 is slid along bridge bar 100 to the desired position and fixed thereat by means of set screws 102. Each pontic base 44 is then screwed up into the undersurface of boss 96 and the assembly tested for proximity of fit of the base 44 to rest light on the gum surface. If the bar part of the assembly does not fit on the occlusal floor of the grooves when the pontic bases touch the gum, then the screw and base are removed and shortened until the screw portion is short enough to permit the transverse beam 100 to rest on the floor of the grooves while the pontic bases lightly touch the gum. Then, mold halves 112 and 114 are secured to the buccal and lingual sides of first and second teeth 54 and 56 by U-shaped clamps 84. The edentulous space between first tooth 54 and second tooth 56 and between mold backing halves 112 and 114 and the mold itself (which was formed previously by wax shaping the two pontics and then using an elastic material like a polysiloxane to pick up the wax shape of the future pontics) is now filled with a pontic forming material. The pontic forming material is made to chemically or catalytically set, whereupon clamps 84 and mold halves 112 and 114 are removed. The remainder of the operation is identical to that previously described in regard to the embodiment of FIGS. 5-10 and need not be described in detail. The end result is shown in FIG. 25. It is noted that the method of FIGS. 1-10 can also be used with this embodiment.

It will be realized that various modifications can be made to the described invention within the scope of the claims herein. For example, boss 32 can be eliminated, with shaft 48 being screw-threaded directly into bridge bar 36, in the first and second embodiments. Also, the present invention can be modified to operate in a cantilevered fashion from only one tooth.

While all of the above embodiments of the invention have related to the formation of at least one pontic in an edentulous space existing between two teeth, the present invention is not so limited. Thus, for example, the present invention can be used to form a pontic with two adjacent teeth, that is, secured to the teeth in a cantilevered fashion, where the edentulous space is posterior to the remaining teeth, and a single pontic tooth is needed to occlude with an opposing tooth.

Referring now to FIGS. 26-34, there is shown a fourth embodiment of the present invention, in which a pontic is formed with a single tooth or preferably two teeth in a cantilevered manner. Specifically, a bridge bar assembly 130 is used which is substantially identical to bridge bar assembly 30 of the first two embodiments, in which elements similar to those of bridge bar assembly 30 are represented by the same numerals augmented by 100, and a detailed description thereof will be omitted herein for the sake of brevity. Basically, bridge bar assembly 130 is identical to bridge bar assembly 30, with the exception that bridge bar 136 is formed with only a first bridge bar section 138 extending from one side of boss 132. In other words, bridge bar section 138 of bridge bar assembly 130 corresponds to bridge bar 38 of bridge bar assembly 30, and there is no bridge bar section corresponding to bridge bar section 40 of bridge bar assembly 30.

Figure 32:
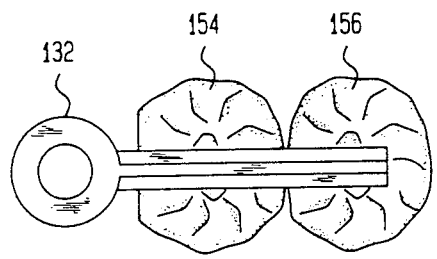
FIG. 32 is a top plan view showing the bridge bar of FIG. 26 with respect to two adjacent teeth.
Figure 31:
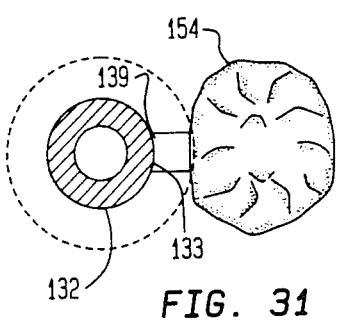
FIG. 31 is a horizontal cross-sectional view of the boss of the bridge bar assembly of FIG. 26 at the level of the bracing section, according to the present invention.

Further, bridge bar section 138 extending from one side of boss 132 is preferably elongated so as to span two adjacent teeth 154 and 156. In this regard, a bracing section 139 is integrally formed with boss 132 toward the gingival side of bridge bar section 138 for providing additional support for the same. In addition, as shown in FIGS. 31 and 32, bracing section 139 is provided so that sufficient pontic forming material is provided about the pontic base and boss. Preferably, bracing section 139 has a width equal to the width of bride bar section 138 and the lower surface 141 thereof is slightly inclined occlusally at a small angle so that there is sufficient space for interdental cleansing if boss 132 is positioned close to pontic base 144. It is also preferable to somewhat flatten the distal side of tooth 154, as shown at 154a in FIGS. 31 and 32, to provide greater strength to the assembly.

The formation of the pontic with bridge bar assembly 130 is similar to that previously described in the second embodiment of the present invention. Specifically, a perforated backing plate 178, as shown in FIG. 30, is formed of a metal material. Backing plate 178 is formed in a substantially U-shaped configuration and has inturned ends 179 at the free ends thereof which face each other. As with the second embodiment, it is necessary to form a mold for the tooth. Thus, a mold forming material 182 is applied to the inner surfaces of backing plate 178. Mold forming material 82 may be a silicone, rubber, polysiloxane or any other impression material and is preferably applied with a thickness of, for example, 3 mm.

Before applying mold forming material 182 to the inner surfaces of backing plate 178, a tooth forming core 183 is positioned adjacent the tooth 154 and held with wax to tooth 154. Tooth forming core 183 may be a preformed core chosen from a number of different configurations. Alternatively, tooth forming core 183 can be formed from a ball of wax configured in the approximate shape of the pontic 152 to be formed. A second alternative is to drill the grooves in the two anterior teeth, place the bridge bar assembly, securing it with wax occlusally to the two teeth, and then shaping the pontic in wax about the shaft and pontic base. The impressions with mold halves are now taken.

Thereafter, backing plate 178 with the mold forming material 182 thereon is positioned against the buccal and lingual sides of tooth forming core 183, and preferably the next two adjacent teeth 154 and 156, both of teeth 154 and 156 being positioned on the same side of tooth forming core 183, as shown in FIG. 33. A U-shaped metal clamp 184 extends over the occlusal surfaces of teeth 154 and 156 and engages the free surfaces of backing plate 178 to secure the latter against the buccal and lingual sides of teeth 154 and 156 and tooth forming core 183. As discussed previously, it is preferable that the mold forming material also be on the sides of backing plate 178 facing away from the teeth in order to provide better grasping thereof by clamp 184. In addition, a lanyard 186 is secured to clamp 184 in the same manner as in the embodiment of FIG. 17.

The mold forming material 182 on backing plate 178 is then permitted to set for approximately three minutes or slightly longer, whereupon clamp 184 is removed to permit removal of the formed mold 190, as shown in FIG. 34. As shown, mold 190 has a U-shaped configuration and is formed of the mold forming material 182 and backing plate 178. The inner surfaces of mold 190 are defined to conform to first and second teeth 154 and 156 and the tooth forming core 183. Thereafter, tooth forming core 183 is removed, and a groove 160 is formed in teeth 154 and 156 in the identical manner as described in the aformentioned embodiments. Bridge bar assembly 130 is then positioned adjacent to teeth 154 and 156 such that bridge bar section 138 is positioned and supported within groove 160. Wherever, possible, the groove would be in two adjacent teeth and the bridge bar extend into both grooves. Then, pontic base 144 is screwed or slid occlusally into the boss and tested for proximity to the gum surface adjacent tooth 154. As previously discussed, the shaft can also be used in a downward adjusting manner if sufficient length extends through the occlusal surface of the boss to hold on to. Lastly, if a vertical sliding element is used instead of a screw adjustment, the vertical component would be slid up and down until the pontic base rested lightly on the gum tissue. A small amount of wax can be used to secure bridge bar section 138 within groove 160.

With bridge bar assembly 130 so positioned, as shown in FIG. 33, mold 190 is positioned about first and second teeth 154 and 156 and about the space surrounding bridge bar assembly 130. Then, U-shaped clamp 154 is again inserted about mold 190 to clamp the same about first and second teeth 154 and 156. The cavity surrounding bridge bar assembly 130, within mold 190, is then filled gradually and completely with a pontic forming material, such as a plastic, or resin composite paste, to a level above the occlusal surfaces of teeth 154 and 156, to form a pontic 152 surrounding boss 132 on bridge bar assembly 130, as shown in FIG. 36. After the pontic forming material is made to set chemically or catalytically to form pontic 152, U-shaped clamp 184 and mold 190 are removed. Accordingly, pontic 152 is formed surrounding bridge bar assembly 130, as shown in FIG. 36, and is assembled with respect to first tooth 154, in a manner similar to that described with the previous embodiments. At this time, any final color modifications on the buccal side can be made with the composite paste, or by available staining techniques. The pontic-bridge bar assembly is removed, the lower surface and sides of the pontic polished and the bridge bar replaced in teeth 154 and 156 for final bonded cementation.

Figure 37:
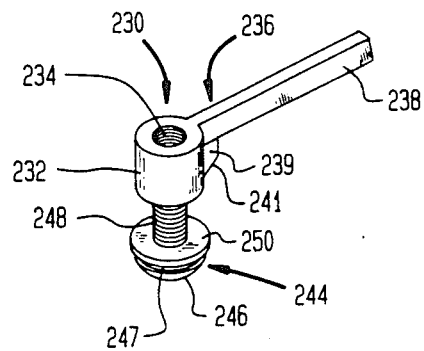
FIG. 37 is a perspective view of a bridge bar assembly according to another embodiment of the present invention, having a groove in the pontic base.
Figure 35:
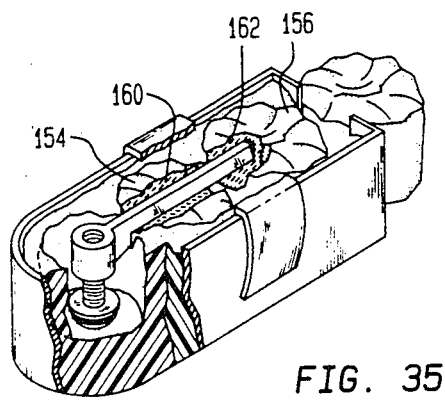
FIG. 35 is a perspective view of the bridge bar assembly of FIG. 26 positioned adjacent two teeth and with the mold as shown in FIG. 34 positioned on opposite sides of the bridge bar assembly and the adjacent teeth and secured together in assembled position.

Referring now to FIG. 37, there is shown a fifth embodiment of the present invention, which is a modification of the aforementioned fourth embodiment of FIGS. 26–34. Specifically, a bridge bar assembly 230 is used which is substantially identical to bridge bar assembly 130 of the fourth embodiment, in which elements similar to those of bridge bar assembly 130 are represented by the same numerals augmented by 100, and a detailed description thereof will be omitted herein for the sake of brevity. Basically, bridge bar assembly 230 is identical to bridge bar assembly 130, with the exception that the convex shaped lower surface 246 of pontic base 244 contains a circumferential groove 247 which is used to provide better retention between pontic base 244 and the formed pontic. This groove should be used on all the pontic bases to improve retention.

Having described specific preferred embodiments of the invention with reference to the accompanying drawings, it will be appreciated that the present invention is not limited to those specific embodiments, and that various changes and modifications can be effected therein by one of ordinary skill in the art without departing from the spirit or scope of the invention as defined by the appended claims.

What is claimed is:

1. A method of forming at least one pontic in situ in an eduntulous space defined between a first tooth and a second tooth posteriorly positioned with respect to said first tooth, and lightly touching the gum surface therebetween, comprising the steps of:
    drilling the distal and occulusal surfaces of said first tooth to form a first groove;
    drilling the mesial and occlusal surfaces of said second tooth to form a second groove;
    positioning a bridge bar assembly including at least one boss and a pontic base adjustably mounted on each said boss, in said edentulous space such that opposite sides of said bridge bar assembly can be fixedly connected in said first and second grooves;
    adjusting said at least one pontic base to a position lightly touching the gum surface in said edentulous space;
    placing a mold about said edentulous space;
    filling said mold with a pontic forming material to form said at least one pontic surrounding said at least one boss on the bridge bar assembly;
    making said pontic forming material set;
    removing said mold;
    polishing the sides and undersurface of each formed pontic; and cementing said bridge bar assembly in said first and second grooves to secure said at least one pontic in said edentulous space.

2. A method according to claim 1 wherein said step of placing includes the step of mounting said mold on said bridge bar prior to placing said mold about said edentulous space.

3. A method according to claim 2 wherein said bridge bar assembly includes a bridge bar extending from opposite sides of said at least one boss and said mold includes first and second mold halves, each mold half having an aperture therein; and said step of mounting includes the step of inserting ends of said bridge bar extending from opposite sides of said at least one boss through the aperture in the respective first and second mold halves, to mount said mold halves on said bridge bar.

4. A method according to claim 3 wherein said first and second mold halves each have a lower section disposed respectively adjacent said gum surface when said bridge bar assembly is positioned between the first tooth and the second tooth; and said step of adjusting includes the step of vertically adjusting said at least one pontic base to a position in light contact with the gingival surface.

5. A method according to claim 1, wherein said step of placing includes the step of placing said mold about said edentulous space and adjacent to at least one of said first tooth and said second tooth.

6. A method according to claim 1, wherein said mold includes a first mold half which is an impression of the buccal side of at least one of said first tooth and said second tooth and the buccal side of said at least one pontic to be formed, and a second mold half which is an impression of the lingual side of at least one of said first tooth and said second tooth and the lingual side of said at least one pontic to be formed; and said step of placing includes the steps of placing said first mold half about said edentulous space and the buccal side of at least one of said first tooth and said second tooth and placing said second mold half about said edentulous space and the lingual side of said at least one of first tooth and said second tooth.

7. A method according to claim 6, further comprising the step of securing together said first and second mold halves adjacent at least one of said first tooth and said second tooth.

8. A method according to claim 1 wherein said mold includes a first mold half which is an impression of the buccal sides of said first tooth and said second tooth and the buccal side of said at least one pontic to be formed, and a second mold half which is an impression of the lingual side of said first tooth and second tooth and the lingual side of said at least one pontic to be formed; and said step of placing includes the steps of placing said first mold half about said edentulous space and the buccal sides of said first tooth and said second tooth and placing said second mold half about said edentulous space and the lingual sides of said first tooth and said second tooth.

9. A method according to claim 8 further comprising the step of securing together said first and second mold halves adjacent said first tooth and said second tooth.

10. A method according to claim 1 further comprising the step of shaping said pontic to achieve proper symmetry with said first tooth and said second tooth.

11. A method according to claim 1, further comprising the step of applying cosmetic veneer to said at least one formed pontic.

12. A method according to claim 1, further comprising the step of making said pontic forming material one of catalytically and chemically set.

13. For use in forming at least one pontic in situ in an edentulous space between a first tooth and a second tooth, a method of forming a first mold half which is an impression of the buccal side of at least one of said first tooth and said second tooth and the buccal side of said at least one pontic to be formed, and a second mold half which is an impression of the lingual side of at least one of said first tooth and said second tooth and the lingual side of said at least one pontic to be formed, said method comprising the steps of:

positioning a tooth forming core in said edentulous space;

applying a mold forming material to a first back plate;

placing said first back plate with said mold forming material thereon against the buccal side of at least one of said first tooth and said second tooth and said tooth forming core;

permitting said mold forming material on said first back plate to harden to form said first mold half;

applying a mold forming material to a second back plate;

placing said second back plate with said mold forming material thereon against the lingual side of at least one of said first tooth and said second tooth and said tooth forming core; and permitting said mold forming material on said second back plate to harden to form said second mold half.

14. A method according to claim 13; further including the step of securing together said first back plate and said second back plate with said mold forming material thereon, adjacent said buccal and lingual sides, respectively, of at least one of said first tooth and said second tooth and said tooth forming core.

15. A method of forming at least one pontic in situ in an edentulous space defined between a first tooth and a second tooth posteriorly positioned with respect to said first tooth, and lightly touching the gum surface therebetween, comprising the steps of:

drilling the distal and occlusal surfaces of said first tooth to form a first groove;

drilling the mesial and occlusal surfaces of said second tooth to form a second groove;

positioning a bridge bar assembly including at least one boss and a pontic base adjustably mounted on each said boss, in said edentulous space such that said bridge bar assembly can be fixedly connected at opposite sides in said first and second grooves;

forming a first mold half which is an impression of the buccal side of at least one of said first tooth and said second tooth and the buccal side of said at least one pontic to be formed;

forming a second mold half which is an impression of the lingual side of at least one of said first tooth and said second tooth and the lingual side of said at least one pontic to be formed;

adjusting said at least one pontic base to a position lightly touching the gum surface in said edentulous space;

placing said first mold half and said second mold half about said edentulous space;

filling said edentulous space between said first mold half and said second mold half with a pontic forming material to form said at least one pontic surrounding said at least one boss on the bridge bar assembly;

making said pontic forming material set;

removing said first mold half and said second mold half;

polishing the sides and undersurface of each formed pontic; and cementing said bridge bar assembly in said first and second grooves to secure said at least one pontic in said edentulous space.

16. A method according to claim 15, wherein said step of forming said first mold half includes the steps of positioning a tooth forming core in said edentulous space, applying a mold forming material to a first back plate, placing said first back plate with said mold forming material thereon against the buccal side of at least one of said first tooth and said second tooth and said tooth forming core, and permitting said mold forming material on said first back plate to harden; and said step of forming said second mold half includes the steps of applying a mold forming material to a second back plate, placing said second back plate with said mold forming material thereon against the lingual side of at least one of said first tooth and said second tooth and said tooth forming core, and permitting said mold forming material on said second back plate to harden.

17. A method according to claim 16, wherein said steps of forming said first mold half and said second mold half each include the step of securing together said first back plate and said second back plate with said mold forming material thereon, against and on said buccal and lingual sides, respectively, of at least one of said first tooth and said second tooth and said tooth forming core.

* * * * *